United States Patent
Takahashi

(10) Patent No.: US 10,718,746 B2
(45) Date of Patent: Jul. 21, 2020

(54) HARDNESS MEASUREMENT METHOD, AND FOULING PREVENTION METHOD FOR HARDNESS-MEASURING DEVICE

(71) Applicant: KURITA WATER INDUSTRIES LTD., Tokyo (JP)

(72) Inventor: Junichi Takahashi, Tokyo (JP)

(73) Assignee: KURITA WATER INDUSTRIES LTD., Tokyo (JP)

( * ) Notice: Subject to any disclaimer, the term of this patent is extended or adjusted under 35 U.S.C. 154(b) by 150 days.

(21) Appl. No.: 15/103,073

(22) PCT Filed: Feb. 10, 2015

(86) PCT No.: PCT/JP2015/053632
§ 371 (c)(1),
(2) Date: Jun. 9, 2016

(87) PCT Pub. No.: WO2015/146327
PCT Pub. Date: Oct. 1, 2015

(65) Prior Publication Data
US 2016/0377586 A1 Dec. 29, 2016

(30) Foreign Application Priority Data

Mar. 28, 2014 (JP) .................................. 2014-070454

(51) Int. Cl.
*G01N 33/00* (2006.01)
*G01N 33/18* (2006.01)
(Continued)

(52) U.S. Cl.
CPC ......... *G01N 33/1853* (2013.01); *G01N 21/78* (2013.01); *G01N 31/00* (2013.01); *G01N 31/22* (2013.01)

(58) Field of Classification Search
CPC .................................................. G01N 33/1853
(Continued)

(56) References Cited

U.S. PATENT DOCUMENTS 3,240,717 A * 3/1966 Johnson ................. G01N 31/22
436/79
3,758,419 A * 9/1973 Hayden ................. C07C 51/353
510/356
(Continued)

FOREIGN PATENT DOCUMENTS

CN 1421695 A 6/2003
CN 1677090 A 10/2005
(Continued)

OTHER PUBLICATIONS

Chung et al. "Selective Cationic Surfactant Detection in Aqueous Solution by Polyurethane Copolymer Linked with Metal Ion Indicator" Fibers and Polymers 2013, vol. 14, No. 12, 2069-2076 (Year: 2013).*
(Continued)

*Primary Examiner* — Christine T Mui
*Assistant Examiner* — Emily R. Berkeley
(74) *Attorney, Agent, or Firm* — Manabu Kanesaka

(57) ABSTRACT

A water hardness-measuring method and a fouling prevention method for hardness-measuring device include adding a colorant containing Eriochrome Black T and/or Calmagite and a sulfate ester-type anionic surfactant having a bonding unit derived from a sulfate ester including an alkyl group having 8 to 18 carbon atoms that may have one or more substituent in its chemical formula to a sample water.

18 Claims, 3 Drawing Sheets

(51) Int. Cl.
*G01N 31/22* (2006.01)
*G01N 31/00* (2006.01)
*G01N 21/78* (2006.01)

(58) Field of Classification Search
USPC .......................................................... 436/79
See application file for complete search history.

(56) References Cited

U.S. PATENT DOCUMENTS

| | | | |
|---|---|---|---|
| 6,228,823 B1 * | 5/2001 | Morinaga | C11D 3/3947 510/175 |
| 2003/0124730 A1 * | 7/2003 | Bailey | G01N 21/643 436/172 |
| 2005/0221499 A1 | 10/2005 | Mitsumoto | |
| 2006/0073999 A1 * | 4/2006 | Sgargetta | C11D 3/168 510/220 |
| 2007/0072305 A1 | 3/2007 | Mitsumoto | |
| 2011/0266496 A1 * | 11/2011 | Mitsuda | A61K 8/34 252/182.3 |

FOREIGN PATENT DOCUMENTS

| | | |
|---|---|---|
| CN | 102539329 A | 7/2012 |
| CN | 102749324 A | 10/2012 |
| JP | H11-064323 A | 3/1999 |
| JP | 2005-315857 A | 11/2005 |
| JP | 2007-093399 A | 4/2007 |
| JP | 2010-090278 A | 4/2010 |
| JP | 2011-174786 A | 9/2011 |
| JP | 2012-214653 A | 11/2012 |
| TW | 200538732 A | 12/2005 |

OTHER PUBLICATIONS

Taiwan Patent Office, "Office Action for Taiwanese Patent Application No. 104109719," dated Aug. 24, 2016.
PCT/ISA/210, "International Search Report for International Application No. PCT/JP2015/053632," dated Apr. 30, 2015.

* cited by examiner

[Fig. 1]
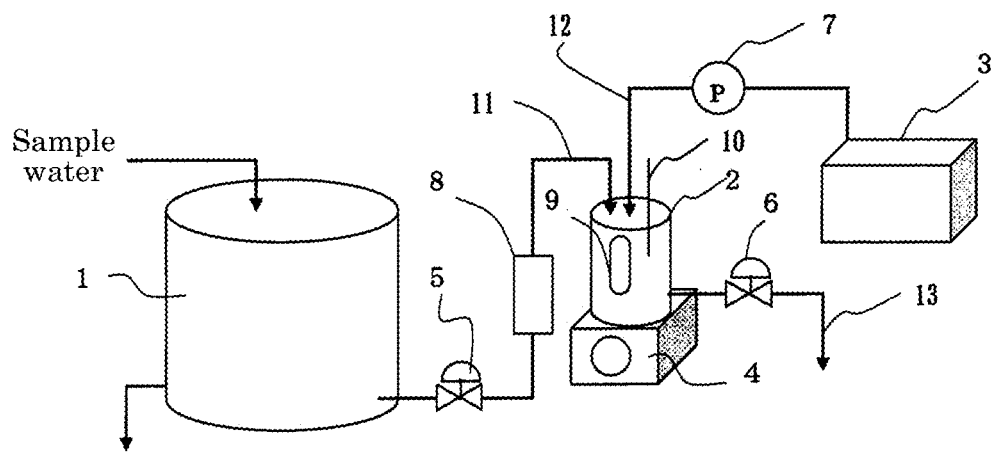
[Fig. 2]
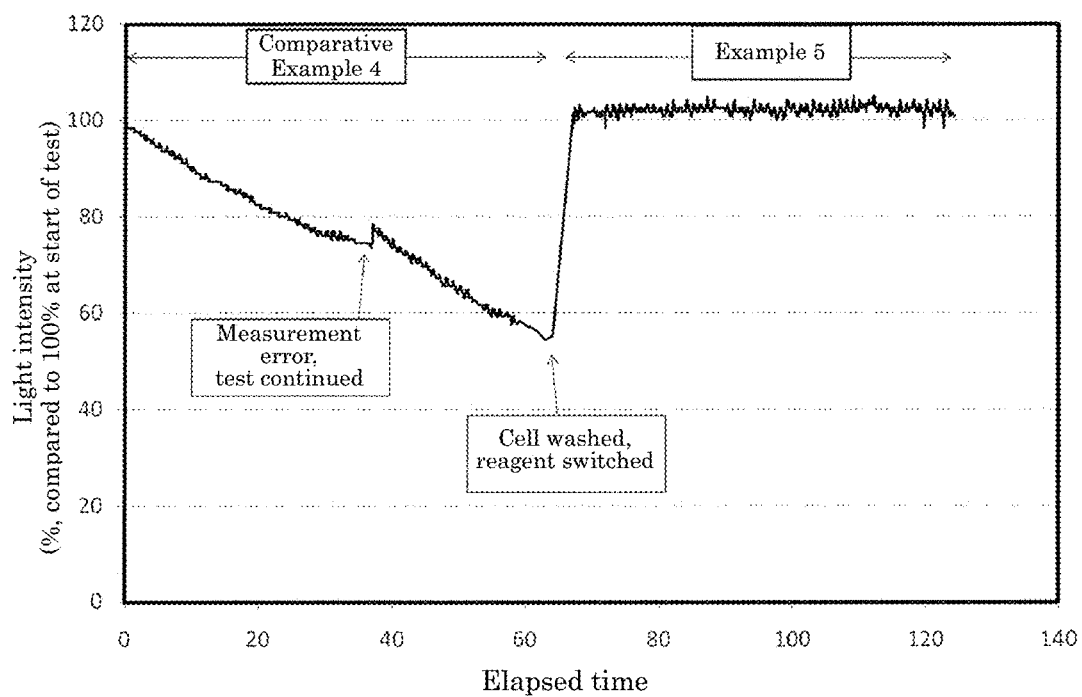

[Fig. 3]
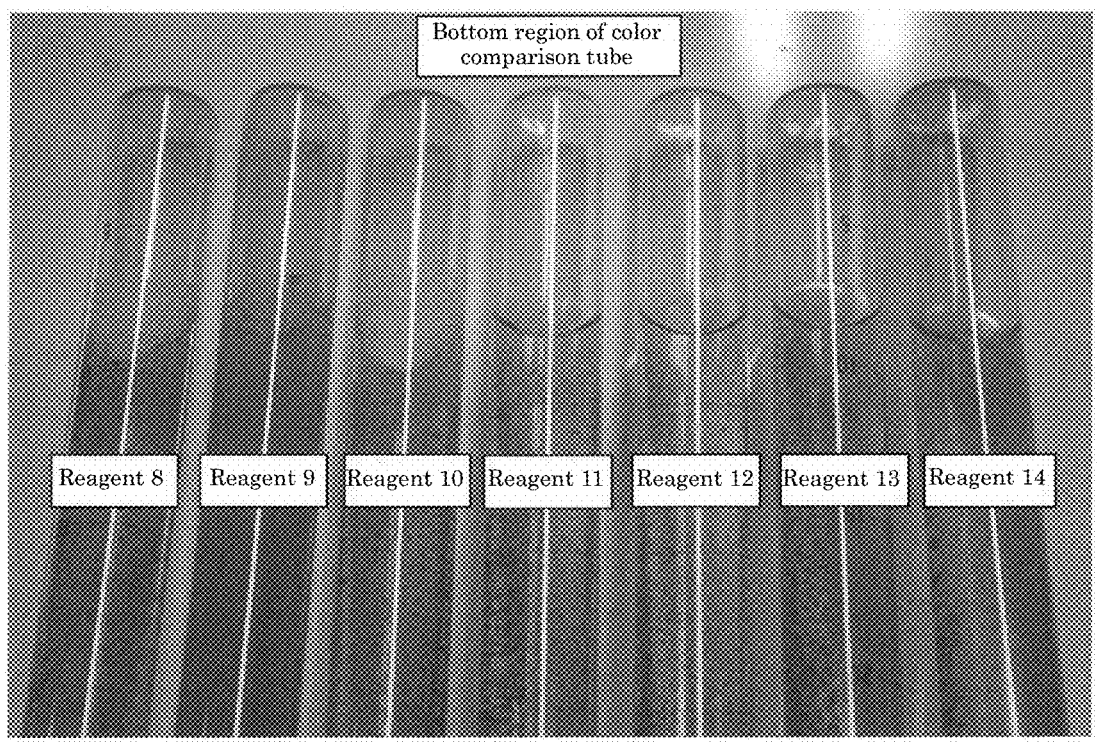

[Fig. 4]
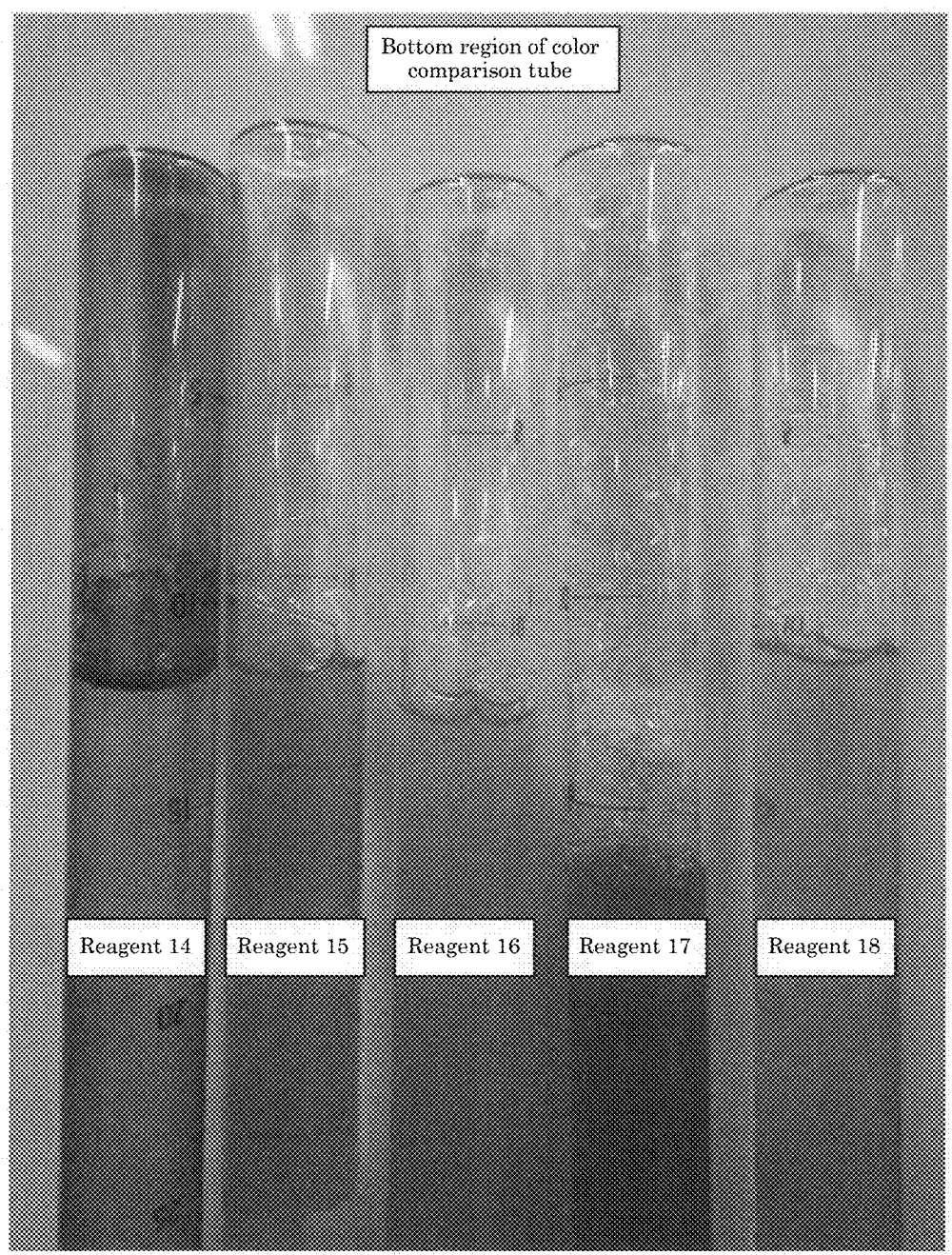

HARDNESS MEASUREMENT METHOD, AND FOULING PREVENTION METHOD FOR HARDNESS-MEASURING DEVICE

RELATED APPLICATIONS

The present application is National Phase of International Application No. PCT/JP2015/053632 filed Feb. 10, 2015, and claims priority from Japanese Application No. 2014-070454, filed Mar. 28, 2014, the disclosure of which is hereby incorporated by reference herein in its entirety.

TECHNICAL FIELD

The present technology relates to a hardness-measuring composition, a hardness-measuring reagent kit, a hardness-measuring method, and a fouling prevention method for hardness-measuring device.

BACKGROUND ART

Apparatuses for removal of hardness components (Ca and Mg ions) contained in raw waters such as industrial and domestic waters have been used for example for pretreatment of water for refrigeration apparatuses such as condensers and boilers and pure water-producing apparatuses for prevention of fouling in the apparatus.

For example, hardness components in raw water are replaced with Na ions in a water-softening apparatus containing ion-exchange resin that is connected to the water-supply line and the softened water obtained is used as feed water.

Because there may be leakage of the hardness components (so-called hardness leakage) for example due to ineffective regeneration or degradation of the ion-exchange resin described above, the leakage of the hardness components is monitored. For example, Patent Document 1 discloses a technology of detecting hardness leakage by using a "hardness indicator comprising Eriochrome Black T (EBT), a pH buffering agent, and a masking agent as main components and additionally Mg-EDTA added thereto".

Recently for reliable or efficient operation of the apparatuses described above, automatic analyzers that analyze the hardness components contained in sample water have been used and the leakage of the hardness components is monitored continuously or periodically (see, e.g., Patent Document 2).

CITATION LIST

Patent Literatures

[Patent Document 1] JP-A No. H11-64323
[Patent Document 2] JP-A No. 2011-174786

SUMMARY OF INVENTION

Technical Problem

There may be substances that deposit in the hardness-measuring device and cause measurement error in sample water and such substances are removed for example by a strainer or a membrane.

However, there may be dissolved substances or very fine particles that are not removable by filtration in water and thus it is desired to prevent measurement error caused by these staining components.

Accordingly, an object of the present technology is to provide a hardness-measuring composition that prevents measurement error caused by deposition of the components contained in sample water in the measurement unit of a water hardness-measuring device.

Solution to Problem

The present technology provides a hardness-measuring composition comprising a colorant containing Eriochrome Black T and/or Calmagite and a sulfate ester-type anionic surfactant.

The sulfate ester-type anionic surfactant may be a surfactant represented by the following General Formula (1);

[C. 1]

(1)

In General Formula (1) above, $R^1$ represents an alkyl, alkenyl, or aryl group having 8 to 18 carbon atoms, M represents a group 1 or 2 element, ammonium, or an alkanolamine; and n is a number of 0 to 10.

Alternatively, the sulfate ester-type anionic surfactant may be a polyoxyethylene alkyl ether sulfate ester salt.

The content of the colorant in the hardness-measuring composition may be 0.05 to 1.0 mass % and the content of the sulfate ester-type anionic surfactant may be 0.1 to 10 mass %.

The hardness-measuring composition may comprise additionally one or more compounds selected from the group consisting of triethanolamine, alkyl alcohols, and glycols.

The present technology also provides a hardness-measuring reagent kit comprising a component A containing a colorant containing Eriochrome Black T and/or Calmagite and a composition B containing a sulfate ester-type anionic surfactant.

The present technology further provides a water hardness-measuring method comprising a step of adding a colorant containing Eriochrome Black T and/or Calmagite and a sulfate ester-type anionic surfactant to sample water.

The present technology further provides a fouling prevention method for hardness-measuring device comprising a step of adding a colorant containing Eriochrome Black T and/or Calmagite and a sulfate ester-type anionic surfactant to sample water in the measurement unit of a water hardness-measuring apparatus.

Advantageous Effects of Invention

It is possible according to the present technology to provide a hardness-measuring composition that prevents measurement error caused by deposition of the components contained in sample water in the measurement unit of a water hardness-measuring device.

BRIEF DESCRIPTION OF DRAWINGS

FIG. 1 is a schematic view explaining the test apparatus used for measuring the hardness of sample water using a hardness-measuring composition.

FIG. 2 is a graph showing the relationship between the light intensity and the test elapsed days when sample water of the same water quality was analyzed using the compositions of Example 2, Comparative Example 4, and Example 5 continuously.

FIG. 3 is a photography showing deposition of staining components in the bottom region of a color comparison tube when the reagents are used in Example 3.

FIG. 4 is a photography showing deposition of staining components in the bottom region of a color comparison tube when the reagents are used in Example 4.

DESCRIPTION OF EMBODIMENTS

Hereinafter, favorable embodiments of the present technology will be described in detail. However, it should be understood that the technology is not limited to the embodiments described below. The present technology may be modified arbitrarily within the scope of the present disclosure.

[Hardness-Measuring Composition]

The hardness-measuring composition in an embodiment of the present technology comprises a colorant containing Eriochrome Black T and/or Calmagite and a sulfate ester-type anionic surfactant.

<Colorant>

The hardness-measuring composition in the present embodiment contains a colorant containing Eriochrome Black T and/or Calmagite as the colorant component.

The Eriochrome Black T (EBT) used as the colorant component, which is the indicator represented by the following Formula (2), is called, for example, sodium 3-hydroxy-4-[(1-hydroxy-2-naphthalenyl)azo]-7-nitro-1-naphthalenesulfonat e, sodium 3-hydroxy-4-[(1-hydroxy-2-naphthyl)azo]-7-nitronaphthalene-1-sulfonate, or Mordant Black 11.

[C. 2]

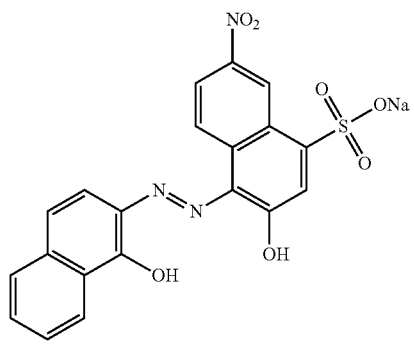

The Calmagite used as the colorant component, which is an indicator having a structure represented by the following Formula (3), is called 3-hydroxy-4-[(2-hydroxy-5-methylphenyl)azo]-1-naphthalenesulfonic acid or 1-(1-hydroxy-4-methyl-2-phenylazo)-2-naphthol-4-sulfonic acid.

[C. 3]

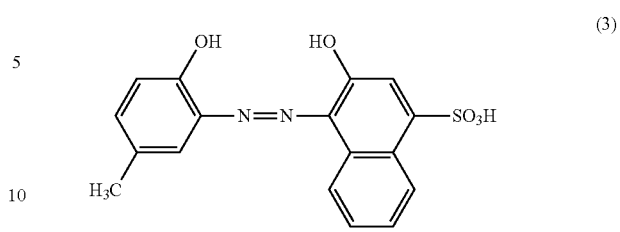

Eriochrome Black T and Calmagite are colorants that discolor from blue to red distinctively by forming chelate compounds with the hardness components such as Ca and Mg contained in the sample water in an alkaline pH range. Eriochrome Black T and Calmagite may be used alone or in combination. They may be used as mixed.

The content of the colorant containing Eriochrome Black T and/or Calmagite is not particularly limited, but preferably 0.05 to 1.0 mass %, more preferably 0.1 to 1.0 mass %, still more preferably 0.1 to 0.5 mass %, in the hardness-measuring composition. When the colorant content is in the range above, it is possible to make the sample water show the color corresponding to the actual hardness, independently of residual chlorine concentration, even if the sample water contains residual chlorine.

<Sulfate Ester-Type Anionic Surfactant>

The hardness-measuring composition in the present embodiment contains a sulfate ester-type anionic surfactant in addition to the colorant component described above.

The sulfate ester-type anionic surfactant is an anionic surfactant having a bonding unit derived from a sulfate ester represented by the following General Formula (4):

$$R^2-O-SO_2-O \qquad (4)$$

In General Formula (4) above, $R^2$ represents a hydrocarbon group that may have one or more substituents. Examples of $R^2$ include, but are not particularly limited to, alkyl groups, alkenyl groups, alkylene groups, aryl groups, arylene groups, and the like.

When $R^2$ is an alkyl or alkenyl group, the carbon number thereof is preferably 8 to 18, more preferably 10 to 16. When $R^2$ is an alkylene group, the carbon number thereof is preferably 1 to 6, more preferably 2 to 4. When $R^2$ is an aryl group, it is preferably a phenyl group. Alternatively when $R^2$ is an arylene group, it is preferably a phenylene group.

The sulfate ester-type anionic surfactant (hereinafter, referred to as "sulfate ester-type surfactant") is preferably an alkyl sulfate ester salt or a polyoxyalkylene alkyl ether sulfate ester salt.

The sulfate ester-type surfactant is preferably that represented by the following General Formula (1):

[C. 4]

$$R^1-O-(CH_2CH_2O)_{\overline{n}}-SO_3M \qquad (1)$$

In General Formula (1) above, $R^1$ represents an alkyl, alkenyl, or aryl group having 8 to 18 carbon atoms; M represents a periodic-table group 1 or 2 element, ammonium, or an alkanolamine; and n is a number of 0 to 10.

In General Formula (1) above, $R^1$ is preferably an alkyl group and $R^1$ preferably has a carbon number of 10 to 16, more preferably 12 to 15. $R^1$ may be a straight chain or a branched chain.

In General Formula (1) above, the counter ion M is preferably Na, K, ammonium ($NH_4$), or triethanolamine ($HN(C_2H_4OH)_3$), more preferably, Na or $HN(C_2H_4OH)_3$.

In General Formula (1) above, the addition molar number n is preferably 0 to 6, more preferably 2 to 4.

The sulfate ester-type surfactant is preferably one or more compounds selected from the group consisting of alkyl sulfate ester salts, polyoxyethylene alkyl ether sulfate ester salts, and polyoxyethylene alkylphenolsulfonic acid salts. More preferably, the sulfate ester-type surfactant used contains at least a polyoxyethylene alkyl ether sulfate ester salt among the surfactants above.

Typical examples of the alkyl sulfate ester salts include lauryl sulfate ester salts such as sodium lauryl sulfate, triethanolamine lauryl sulfate, and ammonium lauryl sulfate; myristyl sulfate ester salts such as sodium myristyl sulfate, triethanolamine myristyl sulfate, and ammonium myristyl sulfate; and the like.

Typical examples of the polyoxyethylene alkyl ether sulfate ester salts include polyoxyethylene lauryl ether sulfate ester salts (laureth sulfate ester salts) such as sodium polyoxyethylene lauryl ether sulfate, triethanolamine polyoxyethylene lauryl ether sulfate, and ammonium polyoxyethylene lauryl ether sulfate; and the like.

The hardness-measuring composition in the present embodiment may contain a commercially available sulfate ester-type anionic surfactant.

Examples of the commercial products of the polyoxyalkylene alkyl ether sulfate ester salts described above include product name "SANDET END" (carbon number of alkyl group: 12 to 15, ethylene oxide addition molar number: 3, counter ion: Na), product name "SANDET EN" (carbon number of alkyl group: 12, ethylene oxide addition molar number: 2, counter ion: Na), and product name "SANDET ET" (carbon number of alkyl group: 12, ethylene oxide addition molar number: 4, counter ion: triethanolamine), produced by Sanyo Chemical Industries Ltd.; product name "Emal 20T" (carbon number of alkyl group: 12, ethylene oxide addition molar number: 3, counter ion: triethanolamine) and product name "Emal 20C" (carbon number of alkyl group: 12, ethylene oxide addition molar number: 3, counter ion: Na) produced by Kao Corp.; and the like.

The content of the sulfate ester-type anionic surfactant described above is not particularly limited, but preferably 0.1 to 10 mass %, more preferably 0.2 to 8.0 mass %, still more preferably 0.3 to 6.0 mass %, in the hardness-measuring composition. When the content of the sulfate ester-type surfactant is in the range above, it becomes possible to prevent fouling of the measurement unit of a hardness-measuring device during measurement of the hardness of water.

<Other Components>
(Benzoic Acid or the Salts Thereof and P-Hydroxybenzoate Esters)

The hardness-measuring composition may comprise benzoic acid or the salt thereof and/or a p-hydroxybenzoate ester in addition to the colorant and the sulfate ester-type surfactant described above.

Examples of the benzoic acid salts include sodium, potassium, and other salts. Examples of the p-hydroxybenzoate esters include those containing an alkyl group having 1 to 5 carbon atoms or an aralkyl group having 7 to 10 carbon atoms.

The alkyl group having 1 to 5 carbon atoms in the p-hydroxybenzoate ester may be a straight-or branched-chain group and examples thereof include methyl, ethyl, n-propyl, isopropyl, n-butyl, isobutyl, sec-butyl, tert-butyl, pentyl, cyclopentyl, and the like.

Alternatively, examples of the aralkyl groups having 7 to 10 carbon atoms include benzyl, methylbenzyl, phenethyl, methyl phenethyl, phenylpropyl, and the like.

Typical examples of the p-hydroxybenzoate esters include methyl p-hydroxybenzoate, ethyl p-hydroxybenzoate, isopropyl p-hydroxybenzoate, butyl p-hydroxybenzoate, isobutyl p-hydroxybenzoate, benzyl p-hydroxybenzoate, and the like.

The hardness-measuring composition may comprise one or more compounds selected from the group consisting of benzoic acid, the benzoic acid salts, and the p-hydroxybenzoate esters described above.

When benzoic acid or a salt thereof and/or a p-hydroxybenzoate ester is contained in the hardness-measuring composition, the content thereof is preferably 0.5 to 10 mass %, more preferably 1 to 5 mass %, in the hardness-measuring composition. When benzoic acid or the like is used at such a content, it is possible, even if the hardness-measuring composition is diluted with sample water by about 20 to 500 times, to inhibit proliferation of microbes in the sample water and make it easier to prevent fouling of the measurement unit in the hardness-measuring device.

(Triethanolamine, Alkyl Alcohol, or Glycol)

The hardness-measuring composition may comprise one or more compounds selected from the group consisting of triethanolamine, alkyl alcohols, and glycols in addition to the colorant and the sulfate ester-type surfactant described above.

Triethanolamine is used for stabilization of the color development of the colorant described above, for example, by bringing the pH of the sample water to around 10. The content of triethanolamine is not particularly limited, but preferably 20 to 90 mass %, more preferably 40 to 80 mass %, in the hardness-measuring composition. When triethanolamine is contained at such a rate, it is possible, even if the hardness-measuring composition is diluted with the sample water by about 20 to 500 times, to stabilize color development of the colorant described above by keeping the pH of the sample water at around 10.

The alkyl alcohol or the glycol is used, for example, as a solvent or an antifreeze liquid for the hardness-measuring composition. Examples of the alkyl alcohols include ethanol, n-propanol, isopropanol, and the like. Alternatively examples of the glycols include ethylene glycol, propylene glycol, diethylene glycol, dipropylene glycol, and the like.

In the present embodiment, the alkyl alcohols and the glycols may be used alone or in combination of two or more.

The content of the alkyl alcohol and glycol is not particularly limited, but preferably 5 to 70 mass %, more preferably 15 to 50 mass %, in the hardness-measuring composition from the viewpoint of the action as the solvent or antifreeze liquid.

<Other Arbitrary Components>

The hardness-measuring composition of the present embodiment may comprise, as needed, other arbitrary components as additives, such as residual chlorine-immobilizing agents, reducing agents, pH buffering agents, chelating agents, masking agents, sensitizers, degradation inhibitors, and antifoaming agents in the range that does not impair the object of the present technology.

(Residual Chlorine-Immobilizing Agent)

When the sample water is sterilized with a chlorine-based bactericide such as sodium hypochlorite, the sample water may contain residual chlorine. When the residual chlorine concentration is approximately 1.5 mg/L or more in the sample water, color development of the hardness-measuring composition containing the colorant may be disturbed.

Accordingly when the residual chlorine is present in the sample water at a concentration of approximately 1.5 mg/L, a residual chlorine-immobilizing agent is preferably added to the hardness-measuring composition.

The residual chlorine-immobilizing agent is a compound generating bound chlorines such as chloramine, chlorimine, and chlorimide in reaction with residual chlorine. Examples of the residual chlorine-immobilizing agents used include primary amines, secondary amines, the salts thereof, ammonium salts, and the like and they can be used alone or in combination of two or more.

Examples of the primary amines include alkyl alcoholamines such as monoethanolamine, straight-chain alkylamines such as butylamine, cyclic alkylamines such as cyclohexylamine, aromatic amines such as aniline, amino acids, and the like.

Examples of the secondary amines include alkyl alcoholamines such as diethanolamine, straight-chain alkylamines such as diethylamine, cyclic alkylamines such as azacyclohexane (piperidine), aromatic amines such as diphenylamine, amino acids, and the like. Among the compounds above, alkyl alcoholamines such as monoethanolamine and diethanolamine are preferable from the viewpoint of stability of the color of the sample water developed corresponding to the hardness of the sample water independently of the residual chlorine concentration.

The content of the residual chlorine-immobilizing agent is not particularly limited, but normally 0.3 to 3.0 mass %, preferably 0.5 to 2.0 mass %, in the hardness-measuring composition. When the content of the residual chlorine-immobilizing agent is in the range above, it is possible to make the sample water have a color corresponding to the actual hardness, independently of the value of the residual chlorine concentration.

(Reducing Agent)

The reducing agent is used, similarly to the residual chlorine-immobilizing agent described above, for prevention of the disturbance to the discoloration of the colorant-containing hardness-measuring composition by the residual chlorine when there is residual chlorine in the sample water.

Examples of the reducing agents include hydroxylamine hydrochloride, ascorbic acid, hydroquinone, cobalt sulfate, sodium isoascorbate, sodium thiosulfate, hydrosulfite, sodium sulfite, tin chloride, aluminum sulfite, methyl ethyl ketoxime, Rongalite, glucose, and the like. These exemplified reducing agents may be used alone or in combination of two or more.

When a hardness-measuring composition containing the reducing agent is used, it is possible to make the sample water have a color corresponding to the actual hardness, independently of the value of the residual chlorine concentration.

The content of the reducing agent is not particularly limited, but preferably 0.3 to 3.0 mass %, more preferably 0.5 to 2.0 mass %, in the entire amount of the hardness-measuring composition.

When the hardness-measuring composition contains a reducing agent, it is favorable to prepare the composition by first mixing the sulfate ester-type surfactant described above with the various additive components used as needed and adding the colorant described above to the mixture.

(pH Buffering Agent)

The pH buffering agent is added for stabilization of color development of the hardness-measuring composition containing the colorant described above, as it adjusts the pH of the sample water to a desired value, independently of the M alkalinity of the sample water.

The pH buffering agent is preferably a combination of an amine selected from the group consisting of primary and secondary amines and a weak base salt. Typical examples of the primary and secondary amines are the same as those described in the section of residual chlorine-immobilizing agent above. The pH buffering agent is also preferably an alkyl alcoholamine such as monoethanolamine or diethanolamine from the viewpoint of stability of the color of the sample water.

The weak base salt is, for example, an ammonium salt, a primary amine salt, a secondary amine salt, or the like. Examples of the ammonium salts include ammonium chloride, ammonium acetate, ammonium sulfate, ammonium bromide, ammonium oxalate, and the like.

Examples of the primary amine salts include acid salts (such as hydrochloride salt, sulfate salt, acetate salt, oxalate salt, and the like) of alkyl alcoholamines such as monoethanolamine, straight-chain alkylamines such as butylamine, cyclic alkylamines such as cyclohexylamine, aromatic amines such as aniline, amino acids, and the like.

Examples of the secondary amine salts include hydrochloride salt, sulfate salt, acetate salt, oxalate salt, and the like of alkyl alcoholamines such as diethanolamine, straight-chain alkylamines such as diethylamine, cyclic alkylamines such as azacyclohexane, aromatic amines such as diphenylamine, amino acids, and the like.

The combination of the amine and the weak base salt is not particularly limited, but preferably a combination of alkyl alcoholamine-ammonium salt from the viewpoint of stability of the color developed in the sample water.

When a pH buffering agent is used, the content of the pH buffering agent is not particularly limited, but preferably 5 to 50 mass %, more preferably 10 to 40 mass %, in the hardness-measuring composition for prevention of its inhibition of other components.

(Chelating Agent)

The chelating agent is added to make the sample water develop color sharply by action of the hardness-measuring composition at around the controlled hardness and thus make it easier to determine whether the hardness component leaks.

The chelating agent used may be an organic chelating agent or an inorganic chelating agent.

Examples of the organic chelating agents include aminocarboxylic acids such as ethylenediamine tetraacetic acid (EDTA), trans-1,2-diaminocyclohexane tetraacetic acid (CyDTA), and o, o'-bis(2-aminoethyl)ethylene glycol tetraacetic acid (GEDTA), and alkali metal salts such as of citric acid and gluconic acid. These chelating agents may be used alone or in combination of two or more.

Examples of the inorganic chelating agents include alkali metal salts of known phosphoric acid compounds such as pyrophosphoric acid, polyphosphoric acid, and metaphosphoric acid. In particular, organic chelating agents are preferable from the viewpoint of preferential chelating efficiency to the hardness component than to the colorant. Among the organic chelating agents, alkali metal salts of aminocarboxylic acids are preferable. Among the alkali metal salts of aminocarboxylic acids, alkali metal salts of EDTA are preferable from the viewpoints of the chelating efficiency and cost effectiveness.

The alkali metal in the alkali metal salt of chelating agent is, for example, Na or K. Examples of the alkali metal salts of EDTA include EDTA-Na, EDTA-K, EDTA-2Na, EDTA-2K, EDTA-3Na, EDTA-3K, EDTA-4Na, EDTA-4K, and the like. Among the EDTA compounds above, EDTA-2Na, EDTA-3Na, and EDTA-4Na are preferable from the viewpoint of solubility when added to the sample water.

The content of the chelating agent is not particularly limited, and it is preferable that the chelating agent is contained in the hardness-measuring composition in an amount that it is added to the sample water at a concentration of [control hardness: 0.1 to 2.0 ppm] for sharp color development at around the control hardness.

The hardness-measuring composition may comprise, as needed additives such as a masking agent, a sensitizer, a degradation inhibitor, an antifoaming agent, and the like in addition to the residual chlorine-immobilizing agent, reducing agent, pH buffering agent, and chelating agent described above.

The masking agent stabilizes the color developed in the sample water by complexing with interfering ions such as Fe, Mn, and Al present in the sample water. Examples of the masking agents include triethanolamine, KCN, and the like. In particular triethanolamine is used favorably from the viewpoint of the safety when the sample water is discharged.

The sensitizer increases the color-developing efficiency of the sample water by substituting $Ca^{2+}$ ions present in the sample water with $Mg^{2+}$ ions and, for example, EDTA-Mg is used favorably. The degradation inhibitor is added for prevention of degradation of the colorant when the hardness-measuring composition is stored at a high temperature of 50° C. or higher and, for example, potassium sorbate is used favorably.

The antifoaming agent is added to prevent foaming of the sample water placed in a measurement container and, for example, a nonionic surfactant is used favorably.

The form of the hardness-measuring composition is not particularly limited and may be liquid, solid, or semi-solid. It is favorably liquid, as it is easier to prepare such a reagent.

The form of the hardness-measuring composition is more preferably a single-liquid composition containing the colorant described above, the sulfate ester-type surfactant described above and, as needed, other components.

It is also possible to use a two-liquid composition consisting of a first reagent containing the colorant described above and, as needed, other components and a second reagent containing the sulfate ester-type surfactant and, as needed, other components. In the case of the two-liquid composition, the first and second reagents are added to the sample water when the hardness of the sample water is determined. In the case of the two-liquid composition, it may be in the form of a "hardness-measuring reagent kit," as will be described below.

Measurement of the hardness of the sample water with the hardness-measuring composition is performed by observing the color change of the sample water, and the observation of the color change may be performed, for example, visually or spectrophotometrically.

The color of the sample water is determined by the presence ratio of the chelate compound formed in reaction of the hardness component with the colorant contained in the hardness-measuring composition to the unreacted (free) colorant. Specifically when EBT is used as the colorant, the color of the sample water changes from blue to blue purple and further via red purple to red, as the hardness of the sample water increases.

The hardness-measuring composition is used to monitor leakage of hardness components to softened water caused, for example, by ineffective regeneration or degradation of the ion-exchange resin used in hard water-softening apparatus and to take measures such as regeneration of the ion-exchange resin, maintenance, and others when the concentration of the hardness components in the softened water become higher than a threshold limit value.

The water for hardness determination is not limited to such a softened water discharged from a hard water-softening apparatus, and examples thereof include raw waters supplied to the hard water-softening apparatus, waters supplied to cooling equipment, waters in hot/cold water systems, boiler waters, and the like.

The hardness-measuring composition in the present embodiment described above can be used as a reagent for measurement of water hardness and it can also be used to prevent deposition of staining components such as metal ions and fine particles contained in the sample water in the measurement unit of the water hardness-measuring device. It is thus possible with the hardness-measuring composition to prevent the measurement errors caused by deposition of stains in the analytical cell and sensor regions of a hardness-measuring device.

It is considered that the fouling on the surface of analytical cell is prevented when the hardness-measuring composition is added to the sample water in the measurement unit (analytical cell) of the analyzer, because the sulfate ester-type surfactant contained in the composition disperse the fine particles in the sample water and the deposits generated, as it is adsorbed on the surface thereof. It is thus considered that the fouling on the measurement unit of the hardness-measuring device can be prevented in this way.

The hardness-measuring composition described above can prevent deposition of stains in the measurement unit of hardness-measuring device caused by the substances present as dissolved in water and the fine particles unremovable with filter. It is also possible to use the hardness-measuring composition described above, even when sample water used is, for example, a water directly softened from untreated well water or a low-pH metal-dissolved water such as boiler drain water that is significantly dirtier.

[Hardness-Measuring Reagent Kit]

The hardness-measuring reagent kit in an embodiment of the present technology comprises a composition A containing the colorant containing Eriochrome Black T and/or Calmagite described above and a composition B containing sulfate ester-type anionic surfactant described above.

It is possible to provide it, for example, as a reagent kit comprising a composition A containing the colorant containing Eriochrome Black T and/or Calmagite described above and a composition B containing sulfate ester-type anionic surfactant described above, as they are placed in separate containers. It is possible in such a form for the user to use the kit by adjusting the ratio of the colorant to the surfactant according to the sample water to be analyzed and the hardness-measuring device used.

The hardness-measuring reagent kit preferably contains the "other components" and the "other arbitrary components" described in the section of the hardness-measuring composition above. In this case, these components may be contained in a container separate from those containing the colorant and the sulfate ester-type anionic surfactant described above or in the container for the composition A and/or B described above.

[Hardness-Measuring Method]

The water hardness-measuring method in an embodiment of the present technology comprises a step of adding a colorant containing Eriochrome Black T and/or Calmagite and a sulfate ester-type anionic surfactant to sample water.

In the hardness-measuring method, when the colorant and the sulfate ester-type anionic surfactant are added to the sample water as mixed in the form of the hardness-measuring composition described above, the blending rate is preferably the rate identical with the content described in the section of the "hardness-measuring composition" above.

Also in the hardness-measuring method, the "other components" and the "other arbitrary components" described in the section of the "hardness-measuring composition" above are preferably used. In this case, the blending rates of the "other components" and the "other arbitrary components" are also preferably the rates identical with the content described in the section of the "hardness-measuring composition" above.

The addition amount of the hardness-measuring composition described above is preferably 0.05 to 10 mass %, more preferably 0.1 to 5 mass %, more preferably 0.5 to 3 mass %, in the sample water.

When the hardness-measuring composition is in the liquid form, the addition amount of the hardness-measuring composition to 1 L of sample water may be preferably 0.5 to 100 mL/L, more preferably 1 to 50 mL/L, more preferably 5 to 30 mL/L.

When the colorant and the sulfate ester-type anionic surfactant described above are added to sample water separately, the amount of the colorant added to the sample water may be, for example, about 0.0001 to 0.1 mass %. The amount of the sulfate ester-type anionic surfactant added to the sample water may be, for example, about 0.001 to 1 mass %.

The hardness-measuring method described above may be stored in a hardware resource having a control unit including CPU and the like or a recording medium (e.g., nonvolatile memory (e.g., USB memory), HDD, or CD) of an apparatus for analysis of the hardness component in sample water and executed by the control unit.

[Fouling Prevention Method]

The fouling prevention method in an embodiment of the present technology comprises a step of adding a colorant containing Eriochrome Black T and/or Calmagite and a sulfate ester-type anionic surfactant to sample water in the measurement unit of an apparatus for determination of water hardness (hardness-measuring device).

In executing the fouling prevention method, the blending rate of the colorant to the sulfate ester-type surfactant when they are added as mixed, the addition amount of hardness-measuring composition after mixing to the sample water, and the addition amounts of the colorant and the sulfate ester-type surfactant when added separately are preferably similar to those described in the section of the "hardness-measuring method" above.

The fouling prevention method can prevents effectively fouling of the measurement unit, such as analytical cell region and sensor region, of a water hardness-measuring device by the staining components contained in sample water. In the hardness-measuring device, it is also possible to prevent effectively fouling by deposition of the staining components contained in the sample water also in the channel through which the sample water flows after the colorant and the sulfate ester-type surfactant described above are added thereto (for example, discharge channel).

The present technology may have the following aspects;

[1] A hardness-measuring composition, comprising a colorant containing one or both of Eriochrome Black T and Calmagite, and a sulfate ester-type anionic surfactant.

[2] The hardness-measuring composition described in [1] above, wherein the sulfate ester-type anionic surfactant is a surfactant represented by the following General Formula (1);

(1)

(in General Formula (1) above, $R^1$ represents an alkyl, alkenyl, or aryl group having 8 to 18 carbon atoms; M represents a group 1 or 2 element, ammonium or an alkanolamine; and n is a number of 0 to 10).

[3] The hardness-measuring composition described in [1] or [2] above, wherein the sulfate ester-type anionic surfactant is a polyoxyethylene alkyl ether sulfate ester salt.

[4] The hardness-measuring composition described in any one of [1] to [3] above, wherein the content of the colorant is 0.05 to 1.0 mass % and the content of the sulfate ester-type anionic surfactant is 0.1 to 10 mass %.

[5] The hardness-measuring composition described in any one of [1] to [4] above, further comprising one or more compounds selected from the group consisting of triethanolamine, alkyl alcohols, and glycols.

[6] A hardness-measuring reagent kit, comprising a composition A containing a colorant containing Eriochrome Black T and/or Calmagite and a composition B containing a sulfate ester-type anionic surfactant.

[7] A water hardness-measuring method, comprising a step of adding a colorant containing Eriochrome Black T and/or Calmagite and a sulfate ester-type anionic surfactant to sample water.

[8] A fouling prevention method for hardness-measuring device, comprising a step of adding a colorant containing one or both of Eriochrome Black T and Calmagite, and a sulfate ester-type anionic surfactant to sample water in the measurement unit of a water hardness-measuring apparatus.

EXAMPLES

Hereinafter, the advantageous effects of the present technology will be described more specifically with reference to Examples.

Example 1

FIG. 1 is a schematic view showing a test apparatus for determining the hardness of sample water using a hardness-measuring composition described in Examples and Comparative Examples. The test apparatus has a line 11 for supply of the sample water in sample water tank 1 to hardness-measuring cell 2 via a constant-flow solenoid valve 5 and a flowmeter 8. It also has a line 12 for supply of the composition in hardness-measuring reagent tank 3 to hardness-measuring cell 2 via pump 7.

The hardness-measuring cell 2 has a transparent window 9 and a liquid surface sensor 10 and a revolving rotator driven by a stirrer 4 (not shown in the Figure) on the bottom. The sample water after hardness measurement in the hardness-measuring cell 2 is discharged by a solenoid valve 6 via line 13.

<Preparation of Hardness-Measuring Composition>

Hardness-measuring compositions 1 to 7 in the blending compositions shown in Table 1 were prepared (hereinafter, referred to as "Reagents 1 to 7").

The "SANDET END" in Table 1, which is the name of a product manufactured by Sanyo Chemical Industries Ltd., is specifically a sulfate ester-type anionic surfactant, specifically, sodium polyoxyethylene alkyl ether sulfate (carbon number of alkyl group: 12 to 15, ethylene oxide addition molar number: 3).

The "SANNONIC FN100" and "SEDORAN FF210" in Table 1, which are names of the products produced by Sanyo Chemical Industries Ltd., are nonionic surfactant, specifically, polyoxyalkylene alkyl ethers.

TABLE 1

|  |  | Reagent 1 | Reagent 2 | Reagent 3 | Reagent 4 | Reagent 5 | Reagent 6 | Reagent 7 |
|---|---|---|---|---|---|---|---|---|
| Blending composition (parts by mass) | EBT | 0.2 | 0.2 | 0.2 | 0.2 | 0.2 | 0.2 | 0.2 |
|  | Triethanolamine | 70 | 70 | 70 | 70 | 70 | 70 | 70 |
|  | Ethanol | 25 | 25 | 25 | 25 | 25 | 25 | 25 |
|  | SANDET END | 0 | 0 | 0 | 0.5 | 1 | 3 | 5 |
|  | SANNONIC FN100 | 0 | 3 | 0 | 0 | 0 | 0 | 0 |
|  | SEDORAN FF210 | 0 | 0 | 3 | 0 | 0 | 0 | 0 |

<Test Condition>

The test water (sample water) was condensed water from a boiler operating using the town water of Kimachi-cho, Tochigi, Japan after it was softened. Because the condensed water was obtained by condensing the vapor and collecting the condensed water using copper and iron heat exchanger and pipes, the condensed water had a pH of approximately 5 to 6 and contained iron and copper ions respectively at concentrations of 0.5 to 2.0 mg/L and 0.1 to 0.5 mg/L.

The test water was supplied to the sample water tank 1 continuously, allowing overflow. The test was performed while the fresh sample was supplied continuously.

Nonionic surfactants, which are generally considered to be effective for fouling prevention, were also evaluated, as shown in Table 1 above. As cationic surfactants developed a red purple color even when they were used for a hardness-free sample water, they are not subjected to applicability evaluation.

(Measurement of the Hardness of Sample Water)

The following operations were performed using each of the Reagents 1 to 7.

(1) First, sample water in sample water tank 1 was supplied to hardness-measuring cell 2 having a capacity of 30 mL via flowmeter 8 and line 11, as constant-flow solenoid valve 5 was opened, and the constant-flow solenoid valve 5 was closed when the liquid surface sensor 10 detected that the amount of the sample water supplied reached 20 mL.

(2) The composition (each reagent) in hardness-measuring composition tank 3 was then added via pump 7 to the sample water in hardness-measuring cell 2 in an amount of 100 μL and the mixture was mixed under agitation as the rotator was rotated by stirrer 4.

(3) Subsequently after sufficiently mixing under agitation, the color of the sample water was determined, using a color tone analyzer having a white LED and a RGB photosensor, through a transparent window 9 installed in hardness-measuring cell 2.

(4) The sample water was then discharged from and refilled to the hardness-measuring cell 2 repeatedly ten times, cleaning the internal surface of the cell 2 sufficiently.

(5) The operations (1) to (4) was repeated every 5 minutes.

The appearance of the hardness-measuring cell 2 after the operations continuously performed for 2, 4, and 6 weeks was determined. The results are summarized in Table 2.

TABLE 2

|  | Comparative Example 1 Reagent 1 | Comparative Example 2 Reagent 2 | Comparative Example 3 Reagent 3 | Example 1 Reagent 4 | Example 2 Reagent 5 | Example 3 Reagent 6 | Example 4 Reagent 7 |
|---|---|---|---|---|---|---|---|
| Start of test | No deposition observed, transparent | No deposition observed, transparent | No deposition observed, transparent | No deposition observed, transparent | No deposition observed, transparent | No deposition observed, transparent | No deposition observed, transparent |
| After 2 weeks | Pale brown deposition observed, measurement continued | Trace amount of deposition observed, transparent | Trace amount of deposition observed, transparent | No deposition observed, transparent | No deposition observed, transparent | No deposition observed, transparent | No deposition observed, transparent |
| After 4 weeks | Brown deposition observed, measurement error | Pale brown deposition observed, measurement continued | Pale brown deposition observed, measurement continued | No deposition observed, transparent | No deposition observed, transparent | No deposition observed, transparent | No deposition observed, transparent |
| After 6 weeks | Brown deposition observed, measurement error | Brown deposition observed, measurement error | Brown deposition observed, measurement error | No deposition observed, transparent | No deposition observed, transparent | No deposition observed, transparent | No deposition observed, transparent |
| After 8 weeks | Brown deposition observed, measurement error | Brown deposition observed, measurement error | Brown deposition observed, measurement error | No deposition observed, transparent | No deposition observed, transparent | No deposition observed, transparent | No deposition observed, transparent |

Example 2

<Test Condition>

Another test (Example 2) was then performed, as the test water (sample water) used in Example 1 was changed.

In Example 2, the test water (sample water) used was well water after it was softened. The well water contained a trace amount (0.5 mg/L or less) of iron, manganese, and other metals. A test similar to the measurement of the hardness of sample water described in Example 1 was performed, as the sample water was supplied to a 3L sample water tank continuously at a flow rate of 3 L/h, allowing overflow of the supplied water (overflow water was discarded), while the fresh sample was supplied continuously. The results are summarized in Table 3.

TABLE 3

|  | Comparative Example 4 Reagent 1 | Comparative Example 5 Reagent 2 | Comparative Example 6 Reagent 3 | Example 5 Reagent 4 | Example 6 Reagent 5 | Example 7 Reagent 6 | Example 8 Reagent 7 |
|---|---|---|---|---|---|---|---|
| Start of test | No deposition observed, transparent | No deposition observed, transparent | No deposition observed, transparent | No deposition observed, transparent | No deposition observed, transparent | No deposition observed, transparent | No deposition observed, transparent |
| After 2 weeks | Trace amount of deposition observed, transparent | Trace amount of deposition observed, transparent | Trace amount of deposition observed, transparent | No deposition observed, transparent | No deposition observed, transparent | No deposition observed, transparent | No deposition observed, transparent |
| After 4 weeks | Pale blue deposition observed, measurement error | Pale blue deposition observed, measurement continued | Pale blue deposition observed, measurement continued | No deposition observed, transparent | No deposition observed, transparent | No deposition observed, transparent | No deposition observed, transparent |
| After 6 weeks | Blue deposition observed, measurement error | Blue deposition observed, measurement error | Blue deposition observed, measurement error | No deposition observed, transparent | No deposition observed, transparent | No deposition observed, transparent | No deposition observed, transparent |
| After 8 weeks | Blue deposition observed, measurement error | Blue deposition observed, measurement error | Blue deposition observed, measurement error | No deposition observed, transparent | No deposition observed, transparent | No deposition observed, transparent | No deposition observed, transparent |

Under the test condition, tests were performed continuously in Comparative Example 4 and Example 5 using sample water having the same water quality. The rate of the light intensity, as compared with 100% of the light intensity at the start of test, was plotted against test elapsed days in FIG. 2. In the test, the test was first performed for 60 days using the Reagent 1 of Comparative Example 4 and, after the hardness-measuring cell 2 was cleaned after the 60 days, the test, using the Reagent 4 of Example 5 was performed for 60 days. The light intensity was determined at a wavelength of 660 nm using an absorptiometer manufactured by HACH.

As shown by the results of Examples 1 and 2, when a nonionic surfactant (Reagent 2 or 3), which is generally considered to be higher in effectiveness in preventing fouling, is used, deposition of stains in the hardness-measuring cell 2 was detected by visual observation two weeks after start of measurement and the hardness-measuring cell became in the state of measurement error after 6 and 8 weeks (Comparative Examples 2, 3, 5, and 6).

In contrast, when a sulfate ester-type anionic surfactant was used, deposition of stains in the hardness-measuring cell 2 was not detected by visual observation and the cell was not in the state of measurement error even after 8 weeks (Examples 1 to 4 and 5 to 8). It was thus considered that it is possible to make the measurement unit of a hardness-measuring device resistant to staining and suppress measurement error by adding a hardness-measuring composition containing a sulfate ester-type anionic surfactant to sample water.

Example 3

<Test Condition>

In Example 3, the fouling-preventing effect endowed when the sulfate ester-type anionic surfactant used in Reagent 11 was added to sample water was examined further, using the Reagents 8 to 14 shown in Table 4.

25 mL of pure water was placed in a color comparison glass tube; 20 mg of $Fe_2O_3$ having a particle diameter of 0.5 μm was added thereto; and 0.5 mL of each of the Reagents 8 to 14 was added thereto. The colorant EBT was not added intentionally in this test for accurate examination of staining.

After the color comparison tube was shaken sufficiently with inversion of the tube, it was stored still at room temperature (20 to 25° C.) and the stains deposited in the bottom region of the color comparison tube after one week was examined by visual observation. An upside down photograph of the color comparison tube after storage for 1 week, wherein the bottom region of the color comparison tube is seen on the top, is shown in FIG. 3.

TABLE 4

|  |  | Reagent 8 | Reagent 9 | Reagent 10 | Reagent 11 | Reagent 12 | Reagent 13 | Reagent 14 |
|---|---|---|---|---|---|---|---|---|
| Blending composition (parts by mass) | EBT | 0 | 0 | 0 | 0 | 0 | 0 | 0 |
|  | Triethanolamine | 70 | 70 | 70 | 70 | 70 | 70 | 70 |
|  | Ethanol | 25 | 25 | 25 | 25 | 25 | 25 | 25 |
|  | SANNONIC FN100 | 2 | 0 | 0 | 0 | 0 | 0 | 0 |
|  | SANNONIC FN140 | 0 | 2 | 0 | 0 | 0 | 0 | 0 |
|  | BLAUNON N509 | 0 | 0 | 2 | 0 | 0 | 0 | 0 |
|  | SANDET END | 0 | 0 | 0 | 2 | 0 | 0 | 0 |
|  | SEDORAN FF210 | 0 | 0 | 0 | 0 | 2 | 0 | 0 |
|  | SEDORAN FF220 | 0 | 0 | 0 | 0 | 0 | 2 | 0 |

"SANNONIC FN140" and "SEDORAN FF220" shown in Table 4 above are the names of the products produced by Sanyo Chemical Industries Ltd., and each of them is a nonionic surfactant, sprcifically, polyoxyalkylene alkyl ether.

Alternatively, "BLAUNON N509" shown in Table 4 above is a nonionic surfactant, sprcifically, polyoxyethylene nonylphenyl ether produced by Aoki Oil Industrial Co., Ltd.
<Test Results>

FIG. 3 demonstrates that the deposition amount on the glass surface of the color comparison tube increases in the order of Reagent 11 (containing "SANDET END") <Reagent 12 (containing "SEDORAN FF210") <Reagent 13 (containing "SEDORAN FF220") <Reagent 10 (containing "BLAUNON N509")≈Reagent 8 (containing "SANNONIC FN100") <Reagent 9 (containing "SANNONIC FN140") ≈Reagent 14 (blank).

The test solution containing the reagent in the color comparison tube containing each of the Reagents 8 to 14 was discarded and pure water was added thereto; a light-emitting unit and a light-receiving unit were placed, facing each other, at both sides of the color comparison tube; and, the transmission coefficient of the light that passed through the color comparison tube, when a light having a wavelength of 660 nm was irradiated from the light-emitting unit to the light-receiving unit, was determined. The transmission coefficient of pure water placed in the color comparison tube was determined before the test of Example 3 and, after the test solution containing the reagent in the color comparison tube was discarded after the test, pure water was added to the color comparison tube and the transmission coefficient was determined immediately.

As a result, the Reagent 11-containing color comparison tube had a transmission coefficient of approximately 100%, the Reagent 12-containing color comparison tube approximately 95%, the Reagent 13-containing color comparison tube approximately 85%, the Reagent 10-containing color comparison tube approximately 80%, the Reagent 8-containing color comparison tube approximately 80%, the Reagent 14-containing color comparison tube approximately 70%, and the Reagent 9-containing color comparison tube approximately 65%.

The results in Example 3 confirms that addition of a sulfate ester-type anionic surfactant is effective in preventing fouling by deposition of the staining components contained in the sample water (fouling in the bottom region of the color comparison tube base in this Example).

Example 4

<Test Condition>

In Example 4, fouling in the bottom region of the color comparison tube was examined in a manner similar to Example 3, except that the kind of the surfactant used in the reagent of Example 3 was changed.

Specifically in Example 4, Reagents 15 to 18 wherein "SANNONIC FN100" used in the Reagent 8 of Example 3 was replaced with each of the following surfactants were used.

Reagent 15: product name "Emal 20CM" (sodium polyoxyethylene alkyl ether sulfate), a sulfate ester-type anionic surfactant produced by Kao Corp.

Reagent 16: product name "SANDET LNM" (sodium alkyl sulfate), a sulfate ester-type anionic surfactant produced by Sanyo Chemical Industries, Ltd.

Reagent 17: product name "Emal TD" (triethanolamine laurylsulfate), a sulfate ester-type anionic surfactant produced by Kao Corp.

Reagent 18: product name "Emal TD powder" (sodium higher alcohol sulfate), a sulfate ester-type anionic surfactant produced by Kao Corp.

In Example 4, the fouling-preventing effect when a sulfate ester-type anionic surfactant different in kind from the sulfate ester-type anionic surfactants used in Reagents 8 to 14 of Example 3 is added to sample water was examined using Reagents 15 to 18 above.

25 mL of pure water was placed in a color comparison glass tube; 20 mg of $Fe_2O_3$ having a particle diameter of 0.5 μm was added thereto; and 0.5 mL of each of the Reagents 15 to 18 was added thereto additionally. After the color comparison tube was shaken sufficiently with inversion of the tube, it was stored still at room temperature (20 to 25° C.) and the stains deposited in the bottom region of the color comparison tube after one week was examined by visual observation. An upside down photograph of the color comparison tube after storage for 1 week, wherein the bottom region of the color comparison tube is seen on the top, is shown in FIG. 4.

In FIG. 4, the Reagent 14 (blank) used in Example 3 was also indicated for comparison.

As shown in FIG. 4, in each of the color comparison tubes containing a Reagent 15 to 18, there was almost no deposition detected on the glass surface of the color comparison tube.

The results in Examples 3 and 4 suggest that sulfate ester-type anionic surfactants such as alkyl sulfate ester salts and polyoxyethylene alkyl ether sulfate ester salts are effective in preventing deposition of staining components in the measurement unit of a water hardness-measuring device. Thus, it would be possible to prevent deposition of stains on the measurement unit of a hardness-measuring device and measurement error caused by fouling by using a hardness-measuring composition containing one of these sulfate ester-type anionic surfactants as an active ingredient in measurement of water hardness.

REFERENCE SIGNS LIST

1: Sample water tank
2: Hardness-measuring cell
3: Hardness-measuring reagent tank
4: Stirrer
5: Constant-flow solenoid valve
6: Solenoid valve for discharge of sample water
7: Pump
8: Flowmeter
9: Transparent window
10: Liquid surface sensor
11: Sample water feed line
12: Hardness-measuring reagent feed line
13: Sample water discharge line

The invention claimed is:
1. A water hardness-measuring method, comprising:
a step of adding a colorant containing Eriochrome Black T and/or Calmagite, a polyoxyethylene alkyl ether sulfate ester salt having a bonding unit derived from a sulfate ester represented by the following General Formula (4) and one or more compounds selected from the group consisting of triethanolamine, alkyl alcohols, and glycols, at a same time, to sample water:

$$R^2-O-SO_2-O \qquad (4)$$

wherein R² represents an alkyl group having 8 to 18 carbon atoms that may have one or more substituent; and a step of measuring a hardness of the sample water.

2. The water hardness-measuring method according to claim 1, wherein
the polyoxyethylene alkyl ether sulfate ester salt is a surfactant represented by the following General Formula (1):

$$R^1-O-(CH_2CH_2O)_n-SO_3M \quad (1)$$

wherein R¹ represents an alkyl group having 8 to 18 carbon atoms; M represents a group 1 or 2 element, ammonium, or an alkanolamine; and n is a number from 0 to 10.

3. The water hardness-measuring method according to claim 1, wherein
the content of the colorant is 0.05 to 1.0 mass % and
the content of the polyoxyethylene alkyl ether sulfate ester salt is 0.1 to 10 mass %.

4. A fouling prevention method for hardness-measuring device, comprising:
a step of adding a colorant containing Eriochrome Black T and/or Calmagite, a polyoxyethylene alkyl ether sulfate ester salt having a bonding unit derived from a sulfate ester represented by the following General Formula (4) and one or more compounds selected from the group consisting of triethanolamine, alkyl alcohols, and glycols, at a same time, to sample water in a measurement unit of a water hardness-measuring apparatus so that deposition of staining components contained in the sample water in the measuring unit is prevented:

$$R^2-O-SO_2-O \quad (4)$$

wherein R² represents an alkyl group having 8 to 18 carbon atoms that may have one or more substituent.

5. The water hardness-measuring method according to claim 1, wherein the step of measuring the hardness of the sample water includes observing a color change of the sample water.

6. The water hardness-measuring method according to claim 1, wherein the step of measuring the hardness of the sample water includes observing a color change of the sample water visually or spectrophotometrically.

7. The fouling prevention method for hardness-measuring device according to claim 4, wherein the polyoxyethylene alkyl ether sulfate ester salt added adsorbs fine particles and deposits in the sample water on a surface of the fine particles and the deposits and disperses the fine particles and the deposits.

8. The water hardness-measuring method according to claim 1, wherein the triethanolamine is added with the colorant and the polyoxyethylene alkyl ether sulfate ester salt in an amount of 40 to 80 mass % of a total amount of a composition added to the sample water to stabilize color development of the colorant.

9. The water hardness-measuring method according to claim 8, wherein a content of the colorant is 0.1 to 0.5 mass % of a total amount of a composition added to the sample water.

10. The water hardness-measuring method according to claim 9, wherein a content of the polyoxyethylene alkyl ether sulfate ester salt is 0.3 to 6.0 mass % of a total amount of a composition added to the sample water to prevent fouling of a measurement unit of a hardness-measuring device during measurement of the hardness of the sample water.

11. The water hardness-measuring method according to claim 1, wherein a fouling prevention agent selected from the group consisting of benzoic acid, benzoic acid salts, and a p-hydroxybenzoate ester, in addition to the colorant, the polyoxyethylene alkyl ether sulfate ester salt, is added in an amount of 1 to 5 mass % of a total amount of a composition added to the sample water to prevent fouling of a measurement unit in a hardness-measuring device.

12. The water hardness-measuring method according to claim 1, wherein a residual chlorine-immobilizing agent selected from the group consisting of primary amines, secondary amines, salts thereof, and ammonium salts, in addition to the colorant, the polyoxyethylene alkyl ether sulfate ester salt, and the one or more compounds selected from the group consisting of triethanolamine, alkyl alcohols, and glycols, is added in an amount of 0.5 to 2.0 mass % of a total amount of a composition added to the sample water to make the sample water develop a predetermined color.

13. The water hardness-measuring method according to claim 1, wherein a reducing agent selected from the group consisting of hydroxylamine hydrochloride, ascorbic acid, hydroquinone, cobalt sulfate, sodium isoascorbate, sodium thiosulfate, hydrosulfite, sodium sulfite, tin chloride, aluminum sulfite, methyl ethyl ketoxime, Rongalite, and glucose, in addition to the colorant, the polyoxyethylene alkyl ether sulfate ester salt, and the one or more compounds selected from the group consisting of triethanolamine, alkyl alcohols, and glycols, is added in an amount of 0.5 to 2.0 mass % of a total amount of a composition added to the sample water to make the sample water develop a predetermined color.

14. The water hardness-measuring method according to claim 1, wherein a pH buffering agent selected from the group consisting of primary amines, secondary amines, salts thereof, and ammonium salts, in addition to the colorant, the polyoxyethylene alkyl ether sulfate ester salt, and the one or more compounds selected from the group consisting of triethanolamine, alkyl alcohols, and glycols, is added in an amount of 10 to 40 mass % of a total amount of a composition added to the sample water to stabilize color development of the composition added to the sample water.

15. The water hardness-measuring method according to claim 1, wherein an organic chelating agent selected from the group consisting of ethylenediamine tetraacetic acid (EDTA), trans-1,2-diaminocyclohexane tetraacetic acid (CyDTA), o,o'-bis(2-aminoethyl)ethylene glycol tetraacetic acid (GEDTA), citric acid, and gluconic acid, in addition to the colorant, the polyoxyethylene alkyl ether sulfate ester salt, and the one or more compounds selected from the group consisting of triethanolamine, alkyl alcohols, and glycols, is added in an amount of 0.1 to 2.0 ppm in the sample water to make the sample water develop a predetermined color at a predetermined hardness and to determine whether a hardness component leaks in the sample water.

16. The water hardness-measuring method according to claim 1, wherein EDTA-Mg, in addition to the colorant, the polyoxyethylene alkyl ether sulfate ester salt, and the one or more compounds selected from the group consisting of triethanolamine, alkyl alcohols, and glycols, is added to increase a color-developing efficiency of the sample water.

17. The water hardness-measuring method according to claim 1, wherein potassium sorbate, in addition to the colorant, the polyoxyethylene alkyl ether sulfate ester salt, and the one or more compounds selected from the group consisting of triethanolamine, alkyl alcohols, and glycols, is added to prevent degradation of the colorant when a composition added to the sample water is stored at 50° C. or higher.

18. The water hardness-measuring method according to claim 1, wherein a nonionic surfactant, in addition to the colorant, the polyoxyethylene alkyl ether sulfate ester salt, and the one or more compounds selected from the group consisting of triethanolamine, alkyl alcohols, and glycols, is added to prevent foaming of the sample water.

* * * * *